(12) United States Patent
Tu et al.

(10) Patent No.: US 6,639,122 B1
(45) Date of Patent: Oct. 28, 2003

(54) TRANSGENIC SWINE HAVING HLA-D GENE, SWINE CELLS THEREOF AND XENOGRAFTS THEREFROM

(75) Inventors: Ching-Fu Tu, Chunan Miaoli (TW); Chun-Jean Lee, Taipei (TW); Jang-Ming Lee, Taipei (TW); Kimiyoshi Tsuji, Yokohama (JP)

(73) Assignee: Animal Technology Institute Taiwan (TW)

( * ) Notice: Subject to any disclaimer, the term of this patent is extended or adjusted under 35 U.S.C. 154(b) by 0 days.

(21) Appl. No.: 09/664,846

(22) Filed: Sep. 19, 2000

(51) Int. Cl.$^7$ .................... A01K 67/027; A01K 67/033; A01K 48/00; C12N 15/85
(52) U.S. Cl. .................... 800/17; 800/13; 424/93.2; 424/93.21; 435/455; 435/320.1; 435/325
(58) Field of Search ................... 800/13, 17; 424/93.21, 424/93.2; 435/455, 325, 320.1

(56) References Cited

U.S. PATENT DOCUMENTS 6,030,833 A    2/2000   Sweebach et al.
6,271,436 B1 * 8/2001   Piedrahita et al. ............ 800/21

FOREIGN PATENT DOCUMENTS

WO        10191833 A  *  7/1998

OTHER PUBLICATIONS

C.-F. Tu et al., Transplantation Proceedings, "Successful Generation of Transgenic Pigs for Human Decay–Accelerating Factor and Human Leucocyte Antigen DQ," Aug. 2000, 32, pp. 913–915.*
C.F. Tu et al., Int Surg,"Generation of HLA–DP transgenic pigs for the study of xenotrasplantation," Apr.–Jun.1999, 84, pp. 176–182.*
Logan et al. Potential use of genetically modified pigsn as organ donors for transplantation into humans 1999 26,pp. 1020–1025.*
Nebert et al. How knockout mouse lines will be used to study the role of drug–metabolizing enzymes and their receptors during reproduction and develpment, and in environmental toxicity, cancer, and oxidative stress vol.53pp. 249–245 1997 feb.*
Mullins et al. Perspectives series: Molecular medicine in genetically engineered animals vol. 97,No. 7,Apr. 1996, pp, 1557–1560.*
Hammer et al. Genetic engineering of mammalian embryos 1986 63:269–278.*
Oxford Advanced Learner's Dictionary, A.P. Cowie, Oxford University Press 1989, p. 1301.
Ralph L. Brinster, Howard Y. Chen, Myrna E. Trumbauer, Mary K. Yagle, and Richard D. Palmiter. PNAS 1985; 82: 4438–4442.
Current Protocols in Immunology, 1990, Wiley & Sons, Inc., pp. 7.0.1–7.0.2.

Histocompatibility Antigens, p. 25 and 109, 1995, ed. Wiley–Liss Inc.

Janis Kuby, Immunology. $3^{rd}$ ed. 1997, pp. 555–570.

Tu, C.F., Sato, T., Hagihara, M., et al: Transplant Proc 30: 3502, 1998.

Bach, F.H., Auchincloss, H: Transplantation Immunology. New York: A John Wiley & Sons, Inc., Publication; 1995, p107.

Strom, T.B., Roy–Chaudhury, P. Manfro. R., et al: Current Opinion Imm 8:688, 1996.

M. Hagihara et al., "MLR and Skin Graft Studies . . . Transgenic Mice" in Transplantation Proceedings, vol. 26, No. 2, Apr. 1994, pp967–968.

E. Cozzi et al., "Expression of Human Decay Accelerating Factor in Transgenic Pigs" in Transplantation Proceedings, vol. 26, No. 3, Jun. 1994, pp. 1402–1403.

K.R. McCurry et al., "Human Complement Regulatory . . . from Humoral Injury" in Nature Medicine vol. 1, No. 5, May 1995, pp. 423–427.

W.L. Fodor et al., "Expression of a Functional Human . . . Hyperacute Organ Rejection" in Proc. Natl. Acad. Sci. USA, vol. 91, Nov. 1994, pp. 11153–11157.

Hitomi Sasari et al., "HLA–G Expression Protects . . . Cell–Mediated Xenogeneic Cytotoxicity" in Transplantation, vol. 67, No. 1, Jan. 1999, pp. 31–37.

K. Tsuji et al., "Role of HLA–DP Antigen . . . Using Transgenic Mice" in Transplantation Proceedings, vol. 25, No. 1, Feb. 1993, pp. 136–137.

M. Hagihara et al., "Mixed Lymphocyte Reaction . . . DQ Transgenic Mice" in Transplantation Proceedings, vol. 26, No. 4, Aug. 1994, pp. 1868.

K. Tsuji et al.,"The Role of HIA Class II Antigens/Genes . . . Xeno Transplantation" in Transplantation Proceedings, vol. 26, No. 4, Aug. 1994, pp. 2441–2443.

J.–M Lee et al., "The Effective Antigen . . . Primed Lymphoctye Tests" in Transplantation Proceedings, vol. 32, pp. 2503–2504 Nov. 2000.

\* cited by examiner

Primary Examiner—Anne M. Wehbe'
Assistant Examiner—Janice Li
(74) Attorney, Agent, or Firm—LaRiviere, Grubman & Payne, LLP

(57) ABSTRACT

The invention provides a transgenic swine having a transgene encoding a human HLA-DQ or HLA-DR protein, and the swine cells thereof. The invention also provides a graft derived from the transgenic swine, in particular a graft-organ or a graft-tissue, which is useful for grafting into a human recipient.

5 Claims, 4 Drawing Sheets

Fig. 1 The Eco RI of HLA-D transgenes

Fig. 3
A
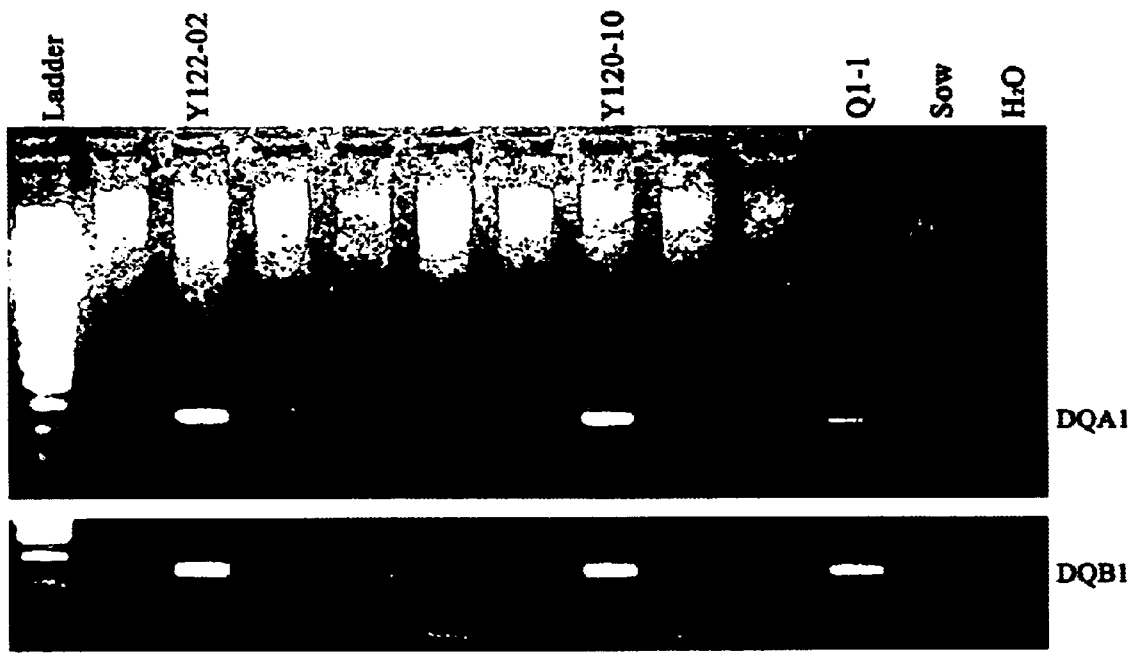
B
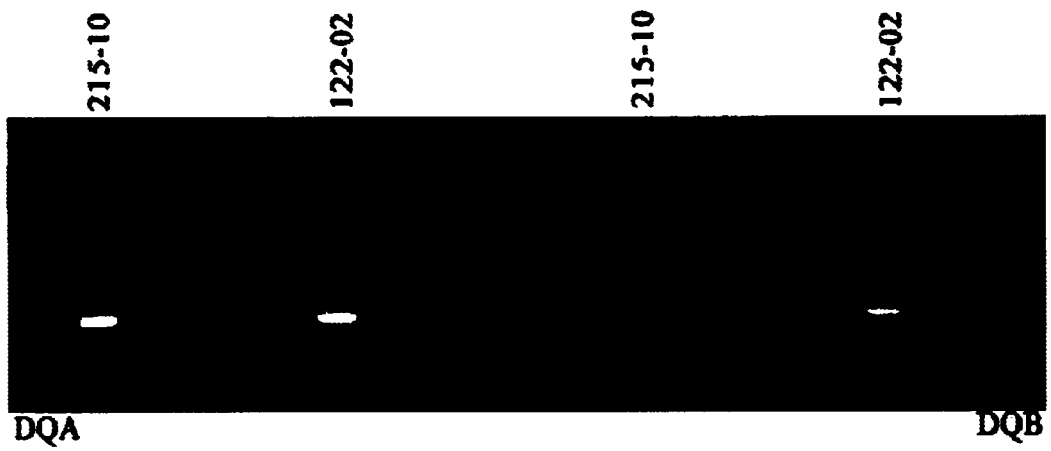

Fig. 4
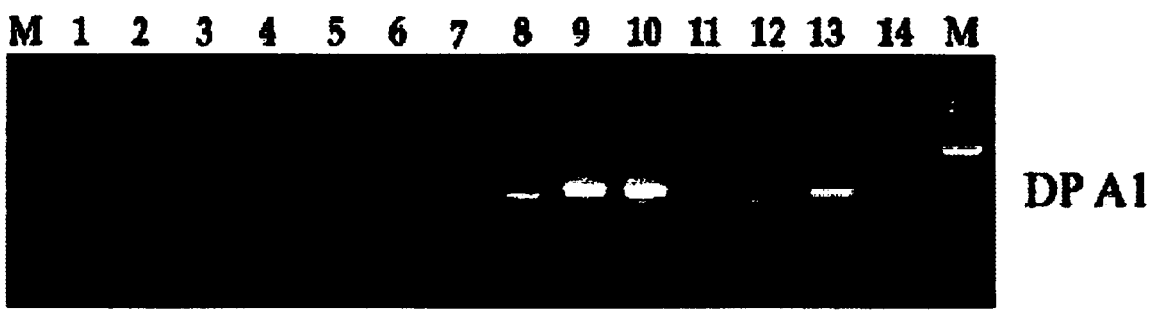
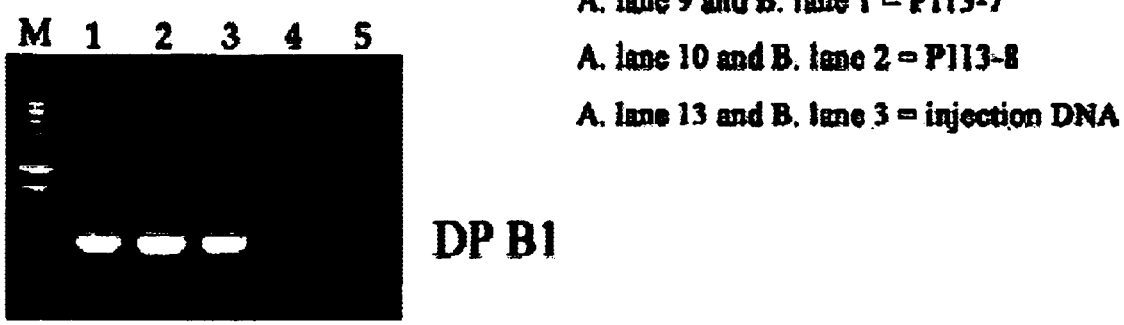
A. lane 9 and B. lane 1 = P113-7
A. lane 10 and B. lane 2 = P113-8
A. lane 13 and B. lane 3 = injection DNA

SEQUENCE LISTING

<160> NUMBER OF SEQ ID NOS: 8

<210> SEQ ID NO 1
<211> LENGTH: 21
<212> TYPE: DNA
<213> ORGANISM: Transgenic Swine Cell DNA

<400> SEQUENCE: 1
ttcctgtggc agcctaagag g               21

-continued

```
<210> SEQ ID NO 2
<211> LENGTH: 20
<212> TYPE: DNA
<213> ORGANISM: Transgenic Swine Cell DNA

<400> SEQUENCE: 2
ccgctgcact gtgaagctct                                              20

<210> SEQ ID NO 3
<211> LENGTH: 26
<212> TYPE: DNA
<213> ORGANISM: Transgenic Swine Cell DNA

<400> SEQUENCE: 3
gtgctgcagg tgtaaacttg taccag                                       26

<210> SEQ ID NO 4
<211> LENGTH: 27
<212> TYPE: DNA
<213> ORGANISM: Transgenic Swine Cell DNA

<400> SEQUENCE: 4
cacggatccg gtagcagcgg tagagtt                                      27

<210> SEQ ID NO 5
<211> LENGTH: 21
<212> TYPE: DNA
<213> ORGANISM: Transgenic Swine Cell DNA

<400> SEQUENCE: 5
gcatgtgcta cttcaccaac g                                            21

<210> SEQ ID NO 6
<211> LENGTH: 27
<212> TYPE: DNA
<213> ORGANISM: Transgenic Swine Cell DNA

<400> SEQUENCE: 6
cacctgcagt cactcacctc ggcgctg                                      27

<210> SEQ ID NO 7
<211> LENGTH: 21
<212> TYPE: DNA
<213> ORGANISM: Transgenic Swine Cell DNA

<400> SEQUENCE: 7
gcggaccatg tgtcaactta t                                            21

<210> SEQ ID NO 8
<211> LENGTH: 20
<212> TYPE: DNA
<213> ORGANISM: Transgenic Swine Cell DNA

<400> SEQUENCE: 8
gcctgagtgt ggttgaaacg                                              20
```

TRANSGENIC SWINE HAVING HLA-D GENE, SWINE CELLS THEREOF AND XENOGRAFTS THEREFROM

BACKGROUND OF THE INVENTION

1. Field of the Invention

The present invention relates to the field of organ transplantation. In particular, the present invention provides transgenic swines and swine cells having human HLA-D genes, which provides organs or tissues for xenotransplantation.

2. Description of the Prior Art

Due to the shortage of human organs or tissues for transplantation, it is desired to seek xenogenic sources. Recently, xenotransplantation of pig organs into humans is a promising strategy for the reason that pigs provide the organs or tissues of a suitable size for xenotransplantation into humans. However, the use of pigs as an organ source is limited because transplantation of a pig graft-organ into a human results in various rejections of the graft-organ including hyperacute, acute and chronic rejections. Recently transgenic pigs were generated to down regulate the pathway of complement activation causing hyperacute rejection, such as the transgenic pigs introduced with a gene encoding human decay accelerating factor (hDAF), see Cozzi et al. (1994) Transplant Proc., 26, 1402–1403; and McCurry et al. (1995) Nat. Med, 1, 423–427; with a gene encoding membrane cofactor protein (MCP), see McCurry et al. (1995); and with a gene encoding CD59, see McCurry et al. (1995); and Fodor et al. (1994), Proc. Natl. Acad. Sci. USA, 91:11153–11157. However, the xenograft of transgenic pig organ into a primate would be rejected due to cell-mediated rejections, including not only hyperacute rejection, but also acute and chronic rejections. All of the rejections must be taken into consideration, in the use of pig organs for xenotransplantation.

The class I molecules of Human leukocyte antigen (HLA-I) were used to generate transgenic pigs for use as an organ source to provide graft-organs without a reduced human nature killer (NK) cell rejection. For instance, Seebach et al. (2000), see U.S. Pat. No. 6,030,833, provided a genetically engineered swine cell having a transgene encoding a human HLA A, HLA B, HLA C or HLA G transgene, wherein expression of the transgene minimizes human nature killer (NK) cell rejection Saaki et al. (1999), Transplantation, 67, 31–37 also disclosed a HLA-G transgenic pig wherein HLA-G expression protects porcine endothelial cells against NK cell-mediated xenogenic cytoxicity.

It is found that HLA-DP typing concordance in allotransplantation is more important than HLA-I matching. HLA-DQ and HLA-DP transgenic mice were generated and studied, such as Tsuji et al. (1993), Transplant Proc., 25, 136–137, Hagihara et al. (1994), Transplant Proc., 26, 967–968; Hagihara et al. (1994), Transplant Proc., 26, 1868; Hagihara et al. (1996), Transpl. Immunol., 4, 220–226; and Tsuji et al. (1994), Transplant Proc., 26, 2441–2443. However, it is not considered that mice are a suitable organ source due to the small sizes of their organs.

Furthermore, Tu et al. (1999), Int. Surg., 84. 176–182, provided two lines of HLA-DP tansgenic pigs to study the role of HLA-DP in xenotransplantation, wherein the integration of the transgene had been confirmed by PCR, DNA sequencing, and Southern blot analysis; and the expression of the transgene had also been proved by RT-PCR. In the HLA-DP transgenic pigs, the expression of HLA-DP antigen on peripheral blood mononuclear cells was reduced, see Tu et al. (1998), Transplant Proc., 30, 3502–35031. The expression of xenogenes were detected in organs or tissues of HLA-DP transgenic pigs, see Lee et al. (2000). Transplant Proc., 32:7; and Lee et al. (1999), a presentation at the 6$^{th}$ Congress of the Asian Society of Transplantation, Singapore, P.310 (Abstract). The function of HLA-DP on xenotransplantation was confirmed by primed mix lymphocyte culture with HLA-DP transgenic pigs' peripheral blood mononuclear transgenic pig cells see Tu et al. (1998), Transplant Proc., 30, 3502–35031.

It is still desired to seek more humanized and suitable organ sources for xenotransplantation into humans.

SUMMARY OF THE INVENTION

One object of the invention is to provide a transgenic swine, which has a human HLA-DQ or HLA-DR transgene, wherein expression of said transgene reduces a xenogenic cellular response between pig and human.

Another object of the invention is to provide an isolated swine cell, which has a human HLA-DQ or HLA-DR transgene, wherein expression of said transgene reduces a xenogenic cellular response between pig and human.

Another further object of the invention is to provide a graft, in particular a graft-organ of a graft-tissue, which is derived from the transgenic swine of the invention.

BRIEF DESCRIPTION OF THE DRAWINGS

FIGS. 2a–b shows the patterns of the PCR products of the transgenic swines introduced with the HLA-DRA1 and HLA-DRB1 genes according to the invention, wherein one live transgenic pig (DR218) carried a transgene HLA-DRB1 (FIG. 2A), and the other (LD146-13) carried both of transgenes HLA-DRA1 and HLA-B1 (FIG. 2B).

FIGS. 3a–b shows the patterns of the PCR products of the transgenic swines introduced with the HLA-DQA1 and HLA-DQB1 genes according to the invention, wherein three of the transgenic pigs (Q1-1, Y122-02 and Y120-10) carried both of HLA-DQA1 and HLA-DQB1 (FIG. 3A), and the other carried HLA-DQA1 only (FIG. 3B).

FIGS. 4a–b shows the patterns of the PCR products of the transgenic swines introduced with the HLA-DPA1 and HLA-DPB1 genes according to the invention, both transgenic pigs (P113-7 and P113-8) carried both of HLA-DPA1 and HLA-DPB1 (FIG. 4A and FIG. 4B).

DETAILED DESCRIPTION OF THE INVENTION

Figure 1:
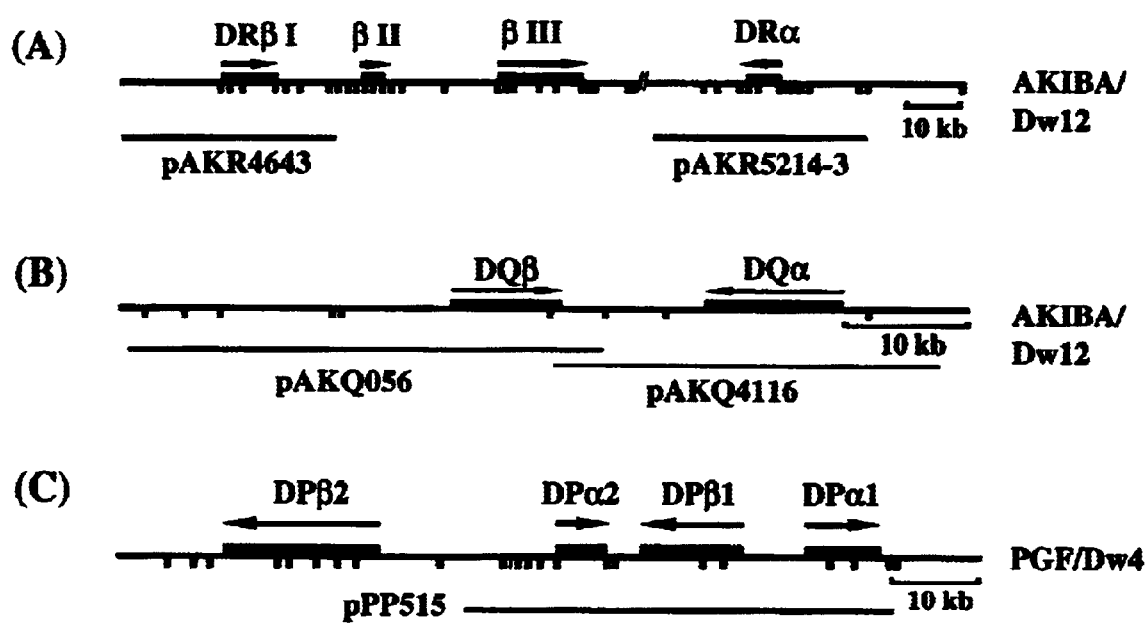
FIGS. 1a–c shows the Eco RI restriction map of HLA-D transgenes, and the plasmids containing the transgenes including pAKR4643 (including an HLA-DRB1 gene encoding DRβ1), pAKR5214 (including an HLA-DRA1 gene encoding DRα), pAKQ056 (including an HLA-DQB1 gene encoding DQβ), PAKQ4116 (including an HLA-DQA1 gene encoding DQα), and pPP515 (including an HLA-DPA1+DPB1 gene encoding DPα1+DPβ1).

The present invention features a transgenic swine containing a human HLA-DQ or HLA-DR transgene, wherein expression of said transgene reduces a xenogenic cellular response between pig and human. It is surprisingly found that the expression of an HLA-DQ transgene reduces a xenogenic cellular response between pig and human.

Preferably, the HLA-DQ transgene is selected from die group consisting of HLA-DQA1 and HLA-DQB1, or the HLA-DQ transgene is a combination of HLA-DQA1 and HLA-DQB1. It is also surprisingly found that the expression of an HLA-DR transgene reduces a xenogenic cellular response between pig and human. Preferably, the HLA-DR transgene is selected from the group consisting of HLA-DRA1 and HLA-DRB1, or the HLA-DR transgene is a combination of HLA-DRA1 and HLA-DRB1.

The term "transgene", as used herein, refers to a nucleic acid sequence encoding a foreign protein, which is partly or entirely heterologous to the transgenic animal or cell into which is introduced. A transgene contains optionally one or more transcriptional regulatory sequences and any other nucleic acid, such as introns, that may be necessary for optimal expression of the selected nucleic acid, all operably linked to the selected nucleic acid, and may have an enhancer sequence. The transgenic gene may be placed into an organism by introducing the foreign gene into embryonic stem (ES) cells, fertilized eggs or early embryos.

The term "foreign gene", as used herein, refers to any gene which is partly or entirely heterologous to the transgenic animal or cell into which is introduced, and is introduced into the genome of an animal by experimental manipulations.

The term "transgenic animal", as used here, refers to any animal in which one or more, or all of the cells of the animal including a transgene. The transgene is introduced into the cell, directly or indirectly by introduction into a precursor of the cell, through genetic manipulation such as by microinjection or infection with a vector (such as a plasmid). In the invention, a transgenic swine was generated by an introduction of a transgene or two transgenes.

The term "transgenic swine cell", as used herein, refers to a swine cell containing a transgene.

The term "vector", as used herein, refers to a nucleic acid molecule capable of transporting another nucleic acid to which it has been linked. A vector, such as a plasmid, is preferably capable of directing the expression of genes to which they are operably linked.

The term "operably linked" means that a selected DNA fragment, such as a gene encoding HLA-II protein, I sin proximity with a transcriptional regulatory sequence, to allow the regulatory sequence (such as a promoter) to regulate expression of the selected DNA fragment.

The term "transcriptional regulatory sequence" refers to a DNA sequence, such as an initiation signal, an enhancer, and a promoter, which induces or controls transcription of a protein coding sequence, which it is operably linked.

The term "graft", as used herein, refers to a body part such as bone or skeletal matrix; an organ such as a heart, lung, liver and kidney; a tissue such as skin, intestines, endocrine glands; and cells such as blood cells, hematopoietic stem cells, and brain cells.

The term "hematopoietic stem cells", as used herein, refers to cells, such as bone marrow cells, fetal or neonatal liver or spleens cells or cord blood cells, which are capable of developing into mature myeloid and/or lymphoid cells.

The term "xenograft", as used herein, refers to a graft used for xenogenic transplantation.

Transgenes

According to the invention, HLA-D transgenes were used, in particular HLA-DQ and HLA-DR; such as HLA-DRA1, HLA-DRB1, and the combination of HLA-DRA1 and HLA-DRB1, HLA-DQA1, HLA-DQB1 and the combination of HLA-DQA1 and HLA-DQB1. The of HLA class II region gene sequences, including HLA-DQ and HLA-DR sequences, have been published in the WIIO Nomenclature reports. The sequence alignments along with a complete list of original references are available in computer readable format via the World Wide Web. The Eca RI restriction map of the HLA-DRA1, HLA-DRB1, HLA-DQA1, HLA-DQB1, and HLA-DPA1+B1 transgenes are shown in FIG. 1.

Transgenic Swine

According to the invention, the transgenic swine may be conveniently obtained by introducing the transgene directly or indirectly into a precursor of the cell of the swine through genetic manipulation such as by microinjection or infection with a vector, such as a plasmid.

Transgenic Swine Grafts

The invention provides transgenic swine cells, such a blood cells, hematopoietic stem cells, and brain cells containing the transgene, which may be conveniently obtained from the transgenic swine of the invention.

According to the invention, the transgenic swine may be used as a xenograft source for transplantation. In a preferable embodiment of the invention, a graft-organ, including kidney, liver, heart pancreas and lung, was derived from swine of the invention. In another preferable embodiment of the invention, a graft-tissue, including skin, intestines, endocrine glands, islet cells or islets, stem cell, bone marrow and vascular tissue, was derived from the transgenic swine of the invention. Because the expression of the transgenes of the invention reduced xenogenic cellular response between pig and human, the xenografts derived from the transgenic swines of the invention are useful for grafting into a human recipient.

The invention could be practiced by using, unless otherwise indicated. techniques, which are within the skill of the art. The conventional techniques are illustrated in the literature, such as *Molecular Cloning A Laboratory Manual*, by Sambrook et al., (Cold Spring Harbor Laboratory Press); *Culture of Animal Cells* (R. I. Freshney. Alan R. Liss, Inc., 1987); *Gene Transfer Vectors for Mammalian Cells*, (J. H. Miller and M. P. Calos eds., 1987, Cold Spring Harbor Laboratory Press).

All methods and materials similar or equivalent to those described herein can be used in the practice of the invention. All publications mentioned herein are incorporated by reference. The following Examples are offered by way of illustration and not by way of limitation.

EXAMPLES

Animals and Treatment

Pure breed Landrace (L), Yorkshire (Y), Durco (D) or their cross-bred (LY) gilts being at least seven and half months old were used. The animals were fed with 1.0 to 1.2 kg commercial feed twice per day and water ad libitium. Sows in lactation were fed with lactation feed and water ad libitium. The transgenic piglets were weaned at 28–56 days after delivered.

All embryos donor and recipient gilts were synchronized by feeding Regumate® (containing 0.4% altrenogest; 20 mg/day; Hoechst UK) mixed with commercial feed in the morning for 15 days, superovulated by injection of PMSG (1500–2000 IU, i.m., China Chem. And Pharm., Taiwan) at 24 hrs after the last feeding Regumate® and injection of hCG *1250–1750 IU, i.m., China Chem. And Pharm., Taiwan) at 76–78 hrs after the injection of PMSG, and mated by artificial insemination with pure breed L, Y, or D boars' fresh-diluted semen at 24–36 hrs after the injection of hCG.

At 54–56 hrs after the injection of hCG, the donor pigs were surgically operated to flush fertilized eggs from the fallopian tubes with 20 ml Dubacos-PBS (Gibco/BRL, USA) with 0.4% BSA (Fraction V. Sigma, USA) into a dish. Before operation, pigs were fasted overnight, and were calmed by injection (i.m.) with 5 ml sterinil (2 mg/kg, Janssen Pharmaceutical, Belgium) and 10 ml atropine sulfate 90.04 mg/kg, China Chem. And Pharm., Taiwan). Then, they were initially anaesthetized by injection of sodium pentobarbitone (10 mg/kg, Abbott Australasia Pty Ltd., Australia) into an ear vein. Anaesthesia was maintained throughout the operation via a closed-circuit system using 4% halothene (ICI Ltd., USA) in an oxygen gas transferred into the fallopian tube of other synchronized foster pigs by surgical methods with the same procedures as for donors. Until piglets were delivered, the piglets' ear or tail tissues were taken to extract their genomic DNA for analysis.

Gene Transfer

The injection of HLA-DR DNAs was mediated through two plasmids, pAKR5214 (DRA1 from AKIBA/Dw12) and pAKR4643 (DRB1 from AKIBA/Dw12), that of HLA-DQ DNAs was mediated through two plasmids, pAKQ4116 (DQA1 from AKIBA/Dw12) and pAKQ56 (DQB1 from AKIBA/Dw12), and that of HLA-DPw4.1 DNAs was mediated through one plasmid, pPP515 (DPA1+DPB1 from PGF/Dw4). The genomic clones of DR and DQ were obtained from AKIBA cell line, that of DP were obtained from PGF cell line; linearized by Mlu I (Toyobo, Japan) for DRA1, DRB1 and DQA1 clones; or linearized by PvuI (Toyobo, Japan) for DQB1 and DP clones.

The DNAs used for injection were diluted with T.E. buffer (10 mM Tris.HCl 0.1 mM EDTA, pH=7.4) to 5 ng/$\mu$l for DR clones, 2 ng/$\mu$l for DQ clones and 2 ng/$\mu$l for DP clones, respectively.

The fertilized eggs were centrifuged with 23,500×g for 8 min. in room temperature by centrifuge (Hettich EBA 12, Germany) to expose pronuclei. The pig embryos were micromanipulated by Leica mechanical manipulator with differential interference contrast inverted Microscope (ZEISS Axiovert 135, Germany). The transgenes were injected into the pronucleus of new fertilized pig eggs or nuclear of two-cell stage of pig embryos. After about 25 to 30 pig embryos were injected, the embryos were transferred into the fallopian tubes of recipient-synchronized as soon as possible.

Analysis of Transgenes

After Pregnancy of sow completed and piglets were delivered, the ear tissue of live piglets or tail tissues of the stillborn piglets were taken to extract genomic DNAs at the delivery day.

The transgenes were screened by PCR wth DRBI primers:
5'-end: 5'-TTC CTG TGG CAG CCT AAG AGG-3'; SEQ ID NO: 1
3'end: 5'CCG CTG CAC TGT GAA GCT CT-3'; SEQ ID NO: 2

The transgenes were screened by PCR with DQAI primers:
5'-end: 5'-GTG CTG CAG GTG TAA ACT TGT ACC AG-3'; SEQ ID NO: 3
3'end: 5'-CAC GGA TCC GGT AGC AGC GGT AGA GTT-3'; SEQ ID NO: 4

The transgenes were screened by PCR with DQBI primers:
5'-end: 5'-GCA TGT GCT ACT TCA CCA ACG-3'; SEQ ID NO: 5
3'end: 5'-CAC CTG CAG TCA CTC ACC TCG GCG CTG-3'; SEQ ID NO: 6

The transgenes were screened by PCR with DPA exon 2 generic typing primers:

5'-end"5'-GCG GAC CAT GTG TCA ACT TAT-3'; SEQ ID NO: 7
3'end: 5'-GC CTG AGT GTG GTT GAA ACG-3' SEQ ID NO: 8 (XI HLA workshop primers).

The PCR reaction was conducted as follows:
the first denature at 94° C. for 3 min. and 40 cycles of amplification wherein each cycle was denatured at 94° C. for 1 min.;
annealing at 58° C. (DR and DP) or 53° C. (DQ) for 1 min., followed by an extension at 72° C. for 1 min.;

The reaction products were analyzed by 2% agarose gel-electrophoresis. In the PCR screening for DR and DQ, transgenic mice genomic DNAs were used as a positive control. In the DP analysis, a Japanese genomic DNA, which is the same HLA-II types as PGF cell line, was used as a positive control in the PCR analysis and the Southern blotting test.

The genomic DNAs of positive piglets were analyzed by Southern blot with DPA1 specific probe. All transgenic pigs and human genomic DNAs were digested with Hin dIII, Eco RI, Bam HI, Sal I, and PvuI (Promega, USA). After restriction enzyme digestion, the DNAs were separated by 0.8% agarose gel electrophoresis, which took place on 25 V electric field for 16 hours. The DNAs in a gel were denatured by alkaline, transferred onto the nylon membrane by Southern's blotting, and hybridized with PDAI specific probe.

Figure 2:
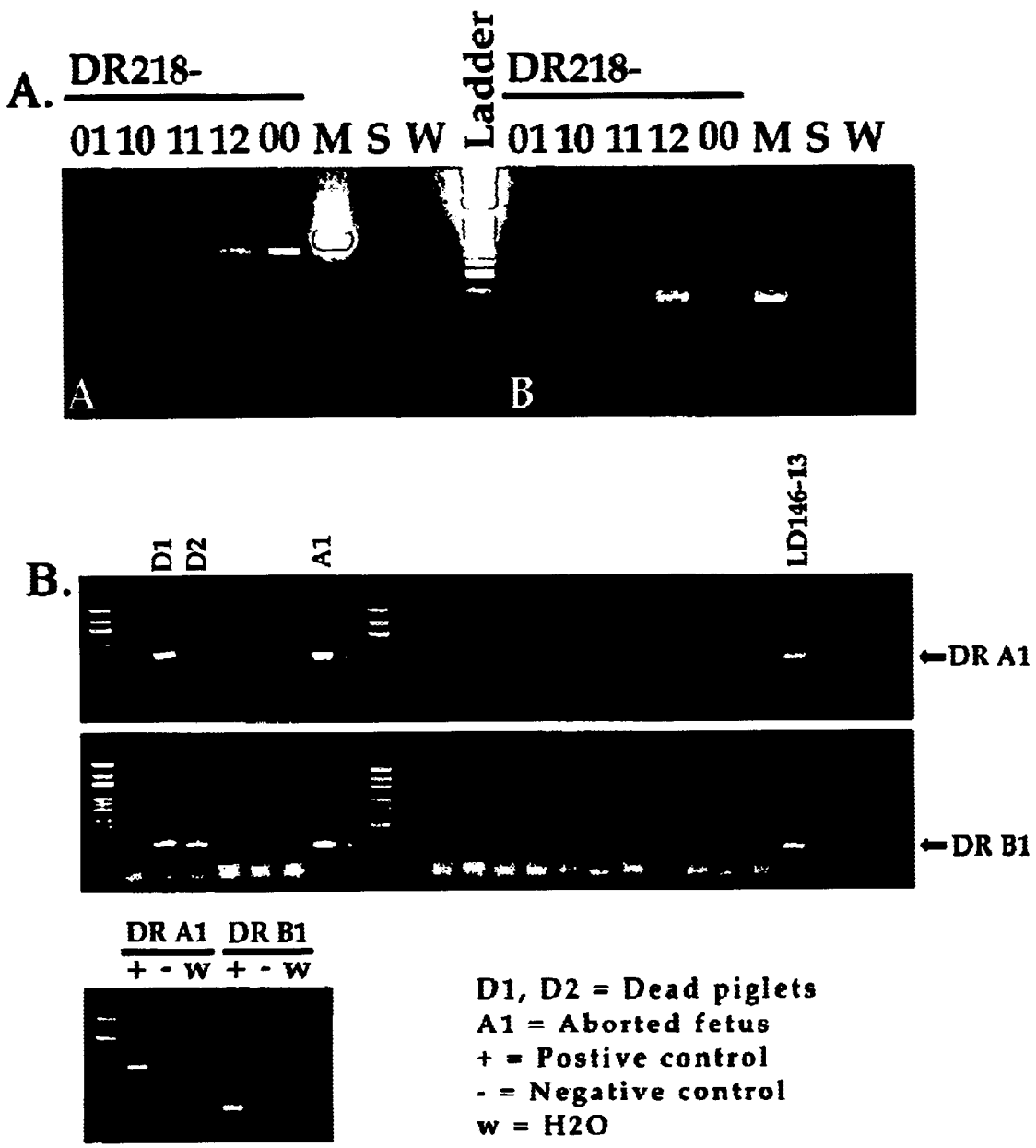
In FIG. 2, D1 and D2 represent two dead piglets; A1 represents an aborted fetus; + represents a positive control; – represents a negative control; and w represents H$_2$O.

The PCR products of DP positive bands were purified by low melting point agarose gel. The patterns of the PCR products of the transgenic swines introduced with the HLA-DRA1 and HLA-DRB1 transgenes were shown in FIG. 2; those with the HLA-DQA1 and HLA-DQB1 transgenes were shown in FIG. 3; and those with the HLA-DPA1 and HLA-DPB1 transgnes were shown on FIG. 4.

They were also sequenced by automatic DNA sequences (ABI PRISMTM 377, PD Applied Biosystems, USA) with dye terminator method. The sequencing primers were the same as PCR primers in DPA1 and DPB1 DNA typing on exon II.

Immunohistochemical Stain

Ear tissues of the HLA-DP, HLA-DQ and HLA-DR transgenic pigs and normally pigs of about one year old were taken to prepare frozen section for detecting the surface antigen of Langerhan cell. Mouse monoclone IgG anti HLA-DQ and HLA-DR were used as a first antibody labeling. A Biotin-labeled goat anti mouse IgG (KPL, USA) was used as a second antibody. The positive reaction was amplified by coagulated with strepavidin-horse radish peroxidase (KPL, USA). The positive signal was detected by the presence of red color of ACE chromagen (Sigma, USA).

Preparation of Primed Lymphocyte Typing (PLT) Reagent

To test antigenicity of HLA-DP w0401 antigen on the surface of lymphocyte of the HLA transgenic pig, a DPw0401 specific PLT reagent was prepared. The responder of the PLT was prepared from the lymphocyte of two healthy adults with identical HLA-DR, DP and DQ except the DPw0401. The lymphocyte of the person without DPw0401 (DPw0401-) was used as responder (Rx) and the person with DPw0401 (DPw0401+) antigen was used as stimulator (B). With mixed culture of Rx and B (RBx), the Rx would develop specific reactivity to the DPw0401 since the Rx and B has identical DR, DP and DQ except the DPw0401 specific PLT reagent. The primed RBx was subsequently co-cultured with the PBMC (peripheral blood mononuclear cell) of HLA-DPw0401 (+) and HLA-DPw0401 (−) human lymphocyte, and HLA-DPw0401 transgenic pig (TG) and its non-transgenic littermate (NTG) respectively. After 40 hours of co-culture, $2\mu$ ci ($^3$H) thymidine (NEN, USA) was added and cultured for further 8 hours. In the Packard system, the result of each culture was given as mean cpm by β-counting for ($^3$H) thymidine incorporated by the cells of the triplicate culture.

Xenogenic MLC

Direct xenogenic MLC was performed with responders of human HLA DP and To test antigenicity of HLA-DPw0401 antigen (+) and HLA-DPw0401 (−) lymphocyte respectively, which was stimulated with mitomycine (Sigma, USA) treated lymphocyte of TG pig and NTG littermate. The responder itself and HLA DPw0401 (+), HLA DPw0401 (−) lymphocyte were also used as stimulators.

Data Analysis and Statistics

The SI (stimulating index) was defined as follows:
a. For PLT: SI=the cpm of ($^3$H) thymidine uptake with various 2nd stimulators/cpm of ($^3$H) thymidine uptake with 2nd stimulator of NTG.

Mann-Whitney test was used to calculate the significance of difference between independent groups.

Results

As shown in FIG. 2A and FIG. 2B, one live transgenic pig (DR218) carried a transgene HLA-DRB1, and the other (LD146-13) carried both of transgenes HLA-DRA1 and HLA-B1. As shown in FIG. 3A and FIG. 3B, three of the transgenic pigs (Q1-1, Y122-02 and Y120-10) carried both of HLA-DQA1 and HLA-DQB1, and the other carried HLA-DQA1 only. The successful generation of human leukocyte antigen DQ (HLA-DQ) transgenic pigs was presented at the $6^{th}$ Congress of the Asian Society of Transplantation, Singapore, 1999 P. 69 (Abstract).

It is shown in FIG. 4 that two transgenic pigs (P113-7 and P113-8) carried both of HLA-DPA1 and HLA-DPB1 (FIG. 4A and FIG. 4B), which were confirmed with Southern bolt analysis and with automatic DNA sequencing on PCR products. The DPw0401 PLT reagents were prepared with the stimulators and responders listed in Table 1.

TABLE 1

HLA II Typing of the Stimulators and Responders for Preparation of PLT Reagents

| Persons/HLA subtypes | HLA-DR | HLA-DQ | HLA-DP |
|---|---|---|---|
| Stimulator 1 | 0301/0301 | 0201/0201 | 0401/0401 |
| Stimulator 2 | 0301/0301 | 0201/0201 | 0401/0401 |
| Responder 1 (205) | 0301/0901 | 0201/0303 | 0504/1701 |
| Responder 2 (204) | 0301/1202 | 0201/0301 | 0501/0501 |
| Responder 3 (245) | 0301/0701 | 0201/0201 | 0301/0301 |
| Responder 4 (263) | 0301/0901 | 0201/0303 | 0501/0501 |

In view of the PLT result, the mean SI with a second stimulator of HLA-DPw0401 (+) human lymphocytes was 6.74±1.46 (n=7), which was significantly higher than those with second stimulators with HLA-DPw0401 (−) control (2.25±0.40, n=7), TG (2.01±0.36, n-7), and NTG (1) (p<0.05 for all). The SI for PLT with $2^{nd}$ stimulators of HLA-DPw0401 (−) human lymphocytes, the mean SIs (±SE) with STIMULATORS OF HLA-DPw0401 (+) and HLA-DPw0401 (−) human lymphocyte are 0.59±0.08 and 0.70±0.07, respectively, which were significantly lower than that with stimulator of NTG (SI=1) (p<0.05). With the stimulators of TG, the SIs of MLC is 0.86±0.13, which is of no significant difference from NTG (SI=1). In the direct xenogenic MLC with responder of HLA-DPw0401 (+) human lymphocyte and TG lymphocytes are 0.87±0.23 and 0.88±0.07, respectively, which was lower than that with stimulators of NTG (p=0.08).

The results demonstrated that the expression of human MHC molecules on the surface of swine cells reduced the xenogenic cellular response between pig and human. In view that the xenogenic cellular response of HLA-DPw0401 (+) transgenic lymphocyte to pig has a tendency to be attenuated when encountered with HLA-DPw0401 (+) transgenic lymphocytes, the HLA-DR and HLA-DQ transgenic pigs could be more humanized and suitable for xenotransplantations.

INDUSTRIAL APPLICABILITY

The present claimed invention finds industrial applicability in the field of providing transgenic swine, cells, tissues and organs having reduced cellular response between swine and humans. The swine, cell, tissues and organs are useful for improving compatibility between swine derived cells, tissues and organs whereby the cells, tissues and organs be used to improve tolerance of xenografts in recipients of xenografts, especially when used in concert with other conventional and/or non-conventional treatments to further improve tolerance of xenografts in recipients. Particularly, the claimed invention finds industrial applicability in xenograft transplantation in human recipients by humanizing the swine xenograft tissue to contain HLA-DQ transgenes to operate with other xenograft rejection suppression therapies to reduce rejection reactions.

What is claimed is:

1. A transgenic swine, whose genome includes an HLA-DQ transgene, wherein said HLA-DQ transgene comprises a combination of human HLA-DQA1 and HLA-DQB1 transgene operably linked to a constitutive promoter, and wherein expression of said transgene reduces a xenogenic cellular response between cells from said transgenic swine and a human subject.

2. An isolated swine cell, whose genome includes an HLA-DQ transgene, wherein said HLA-DQ transgene comprises a combination of human HLA-DQA1 and HLA-DQB1 transgene operably linked to a constitutive promoter, and wherein expression of said transgene reduces a xenogenic cellular response between said cell and a human cell.

3. The swine cell of claim 2, which is obtained from a transgenic swine.

4. A tissue or organ derived from a transgenic swine, whose genome includes an HLA-DQ transgene, wherein said HLA-DQ transgene comprises a combination of human HLA-DQA1 and HLA-DQB1 transgene operably linked to a constitutive promoter, and wherein expression of said transgene reduces a xenogenic cellular response between cells from said transgenic swine and a human subject.

5. The tissue or organ of claim 4, said xenograft being humanized to reduce said xenogenic cellular response in a human recipient.

* * * * *

UNITED STATES PATENT AND TRADEMARK OFFICE
CERTIFICATE OF CORRECTION

PATENT NO.      : 6,639,122 B1                                              Page 1 of 1
DATED           : October 28, 2003
INVENTOR(S)     : Ching-Fu Tu et al.

It is certified that error appears in the above-identified patent and that said Letters Patent is hereby corrected as shown below:

<u>Title page,</u>
Item [56], References Cited, OTHER PUBLICATIONS, in the third reference for "Logan et al.," delete "pigsn" and replace with -- pigs --; and <u>Column 3,</u>
Line 1, delete "die" and replace with -- the --.

Signed and Sealed this

Second Day of March, 2004

JON W. DUDAS
*Acting Director of the United States Patent and Trademark Office*